(12) United States Patent
Trigueiros Da Silva Cunha et al.

(10) Patent No.: US 10,856,778 B2
(45) Date of Patent: Dec. 8, 2020

(54) WRIST RIGIDITY ASSESSMENT DEVICE FOR USE IN DEEP BRAIN STIMULATION SURGERY

(71) Applicant: INESC TEC—INSTITUTO DE ENGENHARIA DE SISTEMAS E COMPUTADORES, TECNOLOGIA E CIÊNCIA, Oporto (PT)

(72) Inventors: João Paulo Trigueiros Da Silva Cunha, Oporto (PT); Pedro Costa, Espinho (PT)

(73) Assignee: INESC TEC—INSTITUTO DE ENGENHARIA DE SISTEMAS E, Oporto (PT)

( * ) Notice: Subject to any disclaimer, the term of this patent is extended or adjusted under 35 U.S.C. 154(b) by 201 days.

(21) Appl. No.: 15/566,436

(22) PCT Filed: Apr. 14, 2016

(86) PCT No.: PCT/IB2016/052135
§ 371 (c)(1),
(2) Date: Oct. 13, 2017

(87) PCT Pub. No.: WO2016/166702
PCT Pub. Date: Oct. 20, 2016

(65) Prior Publication Data
US 2018/0116562 A1   May 3, 2018

(30) Foreign Application Priority Data
Apr. 14, 2015   (PT) .......................... 108366

(51) Int. Cl.
*A61B 5/11* (2006.01)
*A61B 5/00* (2006.01)
*A61B 5/22* (2006.01)

(52) U.S. Cl.
CPC ............ *A61B 5/1124* (2013.01); *A61B 5/002* (2013.01); *A61B 5/1122* (2013.01);
(Continued)

(58) Field of Classification Search
CPC ... A61B 5/1121; A61B 5/1122; A61B 5/1124; A61B 5/11; A61B 5/1125
See application file for complete search history.

(56) References Cited

U.S. PATENT DOCUMENTS 8,187,209 B1   5/2012   Giuffrida
2006/0052726 A1   3/2006   Weisz et al.
(Continued)

FOREIGN PATENT DOCUMENTS

CN   104 127 187 A   11/2014
EP   2 305 118 A1   4/2011
(Continued)

OTHER PUBLICATIONS

Piezoelectric Vibrating Gyroscopes (Gyrostar). Murata Manufacturing Co., Ltd. May 2006. (Year: 2006).*
(Continued)

*Primary Examiner* — Meredith Weare
(74) *Attorney, Agent, or Firm* — Leason Ellis LLP (57) ABSTRACT

It is disclosed an articulation rigidity assessment device for assessing the rigidity of the articulation when a bending motion is imposed to a limb of said articulation around a predetermined rotation axis of the articulation, said device comprising: a one-axis angular velocity sensor for attaching to said limb such that the axis of measurement is parallel to the axis of rotation of the imposed bending motion; a data processor configured to process the signal of the angular velocity sensor and to distinguish between non-rigid and rigid states of the articulation using the processed angular velocity signal. The articulation may be the wrist articulation
(Continued)

of the patient and the limb is the respective hand. The device may comprise a skin-contacting patch for applying to the limb of the patient wherein the one-axis angular velocity sensor is attached to said skin-contacting patch. The skin-contacting patch may be applied to the palm or back of the hand.

17 Claims, 4 Drawing Sheets

(52) U.S. Cl.
CPC ............ *A61B 5/1126* (2013.01); *A61B 5/224* (2013.01); *A61B 5/4519* (2013.01); *A61B 5/4528* (2013.01); *A61B 5/4848* (2013.01); *A61B 5/6806* (2013.01); *A61B 5/6824* (2013.01); *A61B 5/6833* (2013.01); *A61B 5/7246* (2013.01); *A61B 5/7203* (2013.01); *A61B 2562/0219* (2013.01)

(56) References Cited

U.S. PATENT DOCUMENTS

| | | | | |
|---|---|---|---|---|
| 2007/0027631 | A1* | 2/2007 | Cabrera | A61B 5/1107 702/19 |
| 2010/0030119 | A1 | 2/2010 | McNames et al. | |
| 2010/0110169 | A1* | 5/2010 | Zerkin | A61B 5/1121 348/77 |
| 2011/0213275 | A1* | 9/2011 | Boos | A61B 5/1071 600/595 |
| 2012/0139722 | A1* | 6/2012 | Wong | A61B 5/0002 340/539.12 |
| 2012/0157263 | A1* | 6/2012 | Sivak | G06F 3/014 482/4 |
| 2015/0321000 | A1* | 11/2015 | Rosenbluth | A61N 1/0492 607/48 |
| 2016/0262685 | A1* | 9/2016 | Wagner | A61B 5/1123 |
| 2016/0266661 | A1* | 9/2016 | Forsblom | G06F 3/0346 |

FOREIGN PATENT DOCUMENTS

| | | |
|---|---|---|
| WO | WO 2006/102764 A1 | 10/2006 |
| WO | WO 2012/166860 A1 | 12/2012 |
| WO | WO 2013/012625 A1 | 1/2013 |
| WO | WO 2013/123263 A1 | 8/2013 |
| WO | WO 2014/113813 A1 | 7/2014 |

OTHER PUBLICATIONS

C. M. Jarque; A. K. Bera, "Efficient tests for normality, homoscedasticity and serial independence of regression residuals", Economics Letters, (1980), vol. 6, No. 3, pp. 255-259.
N. A. Obuchowski, "Sample size tables for receiver operating characteristic studies", American Journal of Roentgenology, (2000), vol. 175, No. 3, pp. 603-608.
M. B. Shapiro, et. al., "Effects of stn dbs on rigidity in parkinson's disease", Neural Systems and Rehabilitation Engineering,IEEE Transactions, (2007), vol. 15, No. 2, pp. 173-181.
S. Little et. al., "A torque-based method demonstrates increased rigidity in parkinsons disease during low frequency stimulation", Experimental Brain Research, (2012), vol. 219, No. 4, pp. 499-506.
J. Levin, et al., "Objective measurement of muscle rigidity in parkinsonian patients treated with subthalamic stimulation", Movement Disorders, (2009), vol. 24, No. 1, pp. 57-63.
A. L. Benabid et. al, "Deep brain stimulation of the subthalamic nucleus for the treatment of parkinson's disease", the Lancet Neurology, (2009), vol. 8, No. 1, pp. 67-81.
J. W. Lance; R. S. Schwab; E. A. Peterson, "Action tremor and the cogwheel phenomenon in parkinsons disease", Brain, (1963), vol. 86, No. 1, pp. 95-110.
M. K. Mak et al., "Quantitative measurement of trunk rigidity in parkinsonian patients", Journal of Neurology, (2007), vol. 254, No. 2, pp. 202-209.
Y. Kwon et. al., "Quantitative evaluation ofparkinsonian rigidity during intra-operative deep brain stimulation", Biomedical Materials and Engineering, (2014), vol. 24, No. 6, pp. 2273-2281.
Sanger, Terence D., et al., "Classification and Definition of Disorders Causing Hypertonia in Childhood", Pediatrics vol. 111 No. 1 Jan. 2003.
Magrinelli, Francesca et al., "Pathophysiology of Motor Dysfunction in Parkinson's Disease as the Rationale for Drug Treatment and Rehabilitation", Hindawi Publishing Corporation, Parkinson's Disease vol. 2016, Article ID 9832839, 18 pages, Nov. 27, 2015.
Guttman M, Kish SJ, Furukawa Y (2003). Current concepts in the diagnosis and management of Parkinson's disease. CMAJ. Feb. 4, 2003; 168(3): 293-301.
Fearon C, Doherty L, Lynch T (2015). How Do I Examine Rigidity and Spasticity? Mov Disord Clin Pract. Jun. 2015; 2(2): 204. doi: 10.1002/mdc3.12147.

\* cited by examiner

WRIST RIGIDITY ASSESSMENT DEVICE FOR USE IN DEEP BRAIN STIMULATION SURGERY

CROSS-REFERENCE TO RELATED APPLICATIONS

This application is a U.S. National Stage Application under 35 U.S.C. § 371 of International Patent Application No. PCT/IB2016/052135, filed Apr. 14, 2016 which claims priority to Portugal Application No. 108366, filed Apr. 14, 2015, which are hereby incorporated by reference in their respective entireties.

TECHNICAL FIELD

The disclosure pertains to the field of detecting, measuring or recording devices for diagnostic purposes of the movement of a limb. It is disclosed a device for detecting, measuring or recording the muscle rigidity of a subject's articulation while applying passive limb bending motion, quantitatively evaluating the result of the measurement, especially on cogwheel or gear-like rigidity, in particular of the wrist joints.

BACKGROUND

Document JP2010193936 discloses an apparatus for measuring the muscle rigidity of a subject while applying passive upper limb bending motion, and quantitatively evaluating the result of measurement especially on the cogwheel or gear-like rigidity, utilizing a motor with an increased motion torque for passively applying the upper-limb bending motion to the subject and a myogenic potential measuring means for measuring the myogenic potential; and a forearm position measuring means for measuring the position of the forearm by a position convertor with a displacement cable. An analysis value is computed on the digital data obtained by downloading biological information on the myogenic potential, and the muscle rigidity is quantitatively evaluated based on the computed data of the analysis value.

The device of JP2010193936 requires both measurement means for the myogenic potential and the forearm position, thus having increased complexity and unwieldiness as the pictured device clearly shows.

NON-PATENT LITERATURE REFERENCES

[2] M. B. Shapiro, D. E. Vaillancourt, M. M. Sturman, L. V. Metman, R. A. Bakay, and D. M. Corcos, "Effects of stn dbs on rigidity in parkinson's disease," Neural Systems and Rehabilitation Engineering, IEEE Transactions on, vol. 15, no. 2, pp. 173-181, 2007.

[3] A. L. Benabid, S. Chabardes, J. Mitrofanis, and P. Pollak, "Deep brain stimulation of the subthalamic nucleus for the treatment of parkinson's disease," The Lancet Neurology, vol. 8, no. 1, pp. 67-81, 2009.

[4] J. W. Lance, R. S. Schwab, and E. A. Peterson, "Action tremor and the cogwheel phenomenon in parkinsons disease," Brain, vol. 86, no. 1, pp. 95-110, 1963.

[5] Y. Kwon, S.-H. Park, J.-W. Kim, Y. Ho, H.-M. Jeon, M.-J. Bang, S.-B. Koh, J.-H. Kim, and G.-M. Eom, "Quantitative evaluation of parkinsonian rigidity during intra-operative deep brain stimulation," Biomedical materials and engineering, vol. 24, no. 6, pp. 2273-2281, 2014.

[6] J. Levin, S. Krafczyk, P. Valkovi˘c, T. Eggert, J. Claassen, and K. Botzel, "Objective measurement of muscle rigidity in parkinsonian patients treated with subthalamic stimulation," Movement Disorders, vol. 24, no. 1, pp. 57-63, 2009.

[7] S. Little, R. A. Joundi, H. Tan, A. Pogosyan, B. Forrow, C. Joint, A. L. Green, T. Z. Aziz, and P. Brown, "A torque-based method demonstrates increased rigidity in parkinsons disease during low frequency stimulation," Experimental brain research, vol. 219, no. 4, pp. 499-506, 2012.

[8] C. M. Jarque and A. K. Bera, "Efficient tests for normality, homoscedasticity and serial independence of regression residuals," Economics letters, vol. 6, no. 3, pp. 255-259, 1980.

[9] N. A. Obuchowski, "Sample size tables for receiver operating characteristic studies," American Journal of Roentgenology, vol. 175, no. 3, pp. 603-608, 2000

[10] M. K. Mak, E. C. Wong, and C. W. Hui-Chan, "Quantitative measurement of trunk rigidity in parkinsonian patients," Journal of neurology, vol. 254, no. 2, pp. 202-209, 2007.

GENERAL DESCRIPTION

Parkinson's Disease (PD) patients often need Deep Brain Stimulation (DBS) surgery when they become intolerant to drugs or these lose efficiency. A stimulation electrode is implanted in the basal ganglia to promote the functional control of the deregulated dopaminergic motor pathways. The stimulation target is defined by medical imaging, followed by electrophysiological inspection for fine electrode position trimming and electrical stimulation tuning. Intraoperative stimulation of the target and the evaluation of wrist rigidity allows to chose the stimulation parameters which best alleviate PD symptoms without side effects. For that, neurologists impose a passive wrist flexion movement and qualitatively describe the perceived decrease in rigidity under different voltages, based on its experience and with subjectivity. It is disclosed a comfortable and wireless wearable motion sensor to classify the wrist rigidity by: computing a robust signal descriptor from angular velocity values; building a polynomial mathematical model to classify signals using a quantitative continuous scale. The derived descriptor significantly ($p<0.05$) distinguished between non-rigid and rigid states, and the classification model labelled correctly above 80% of the evaluated signals against the blind-agreement of two specialists. Additionally, it is disclosed a methodology to detect cogwheel rigidity from the angular velocity signal with high sensitivity (0.93). The disclosure provides a reliable evaluation of wrist rigidity, improving upon the inherent subjective clinical evaluation while using small, simple and easy to use motion sensor.

Parkinson's Disease (PD) is a neurodegenerative disorder caused by a reduction in the amount of dopaminergic neurons in the basal ganglia. Dopamine has an inhibitory effect on the excitatory signals to the corticospinal motor control system. The decrease of dopamine transmission between neurons causes the motor pathways to remain in an excited state, thus impairing one's mobility. Cardinal symptoms evidenced by PD patients include bradykinesia (slowness), resting tremor, rigidity and postural instability.

Currently, there is no cure for PD, although levodopa and dopamine antagonists temporarily relieve the condition. Unfortunately, these drugs lose efficiency over time, leading to a higher incidence and intensity of the manifested symptoms [2], or patients may become intolerant to the drugs.

High-frequency Deep Brain Stimulation (DBS) of the basal ganglia structures—such as the subthalamic nucleus (STN) and internal globus pallidus (GPi)—is now the preferred surgical option to alleviate PD symptoms. It has been reported to reduce tremor, bradykinesia and, specially, rigidity better than medication alone. The procedure consists in the implantation of a stimulation electrode that promotes the functional inhibition of the excited motor control pathways, resembling the effect of dopamine on the basal ganglia structures.

The stereotactic target of stimulation is defined based on pre-operative medical imaging. Then, the best stimulation site is found by electrophysiological exploration using a tetrapolar electrode. The four contacts on the lead are subsequently inspected while varying the stimulation parameters and testing symptoms and side effects to determine the final placement of the electrode. The wrist rigidity is a reliable feature since it can be measured passively by a trained neurologist and scored using a semi-quantitative scale [3]. Such rigidity hampers the wrist flexion movement, inducing jerky movements of the wrist joint. This resembles the action of a cogwheel [4] and is a relevant clinical feature. This evaluation is often biased by the experience, perception and subjective scale defined by each physician [5], creating the need for an objective and quantitative evaluation methodology.

The existing technology requires complex acquisition setups and has been used to prove the existence of correlation between kinematic measures and UPDRS clinical scores. However, such analysis is done a posteriori and the complexity and invasiveness of the existing systems make them unpractical for intra-OR DBS procedures. A practical, simple and precise system to evaluate wrist rigidity under specific stimulation parameters during DBS surgery and a method to detect cogwheel rigidity from angular velocity data were designed. Such solution significantly reduces the degree of subjectivity of the evaluation and greatly helps in the determination of the optimal stimulation setting.

PD patients rigidity is commonly described using the Unified Parkinsons Disease Rating Scale (UPDRS). For the case of wrist rigidity, the neurologist is asked to grade the passive wrist flexion and extension resistance from absent (0) to severe (4). Consequently, this discrete scale is highly subjective, as mentioned before.

The introduction of motion sensors to measure wrist rigidity in implanted patients is fairly new. The first experimental demonstration of the effectiveness of STN DBS stimulation occurred in 2007 [2]. In this study, the patients were asked to manipulate a lightweight bar in both on and off stimulation states. They later integrated the inertial torque over consecutive angles of the wrist to calculate the work applied, showing statistical significance between both states.

Following that study, [6] objectified muscle rigidity via surface electromyography (EMG) recordings of the biceps and the triceps brachii, with high correlation between measures and UPDRS scores of specialists. More recently, [7] further explored the premises arose by [2], and observed a significant decrease in wrist rigidity under high-frequency DBS while manipulating an aluminium bar. Angular displacement was assessed using a goniometer across the wrist and the force was measured by a strain gauge mounted on the bar. At the therapeutic frequency of stimulation, 130 Hz, increased mobility was shown. In 2014, [5] evaluated the wrist rigidity during intra-operative DBS by measuring several biomechanical properties. High correlation rates were found between the viscous damping and UPDRS clinical scores.

Figure 1:
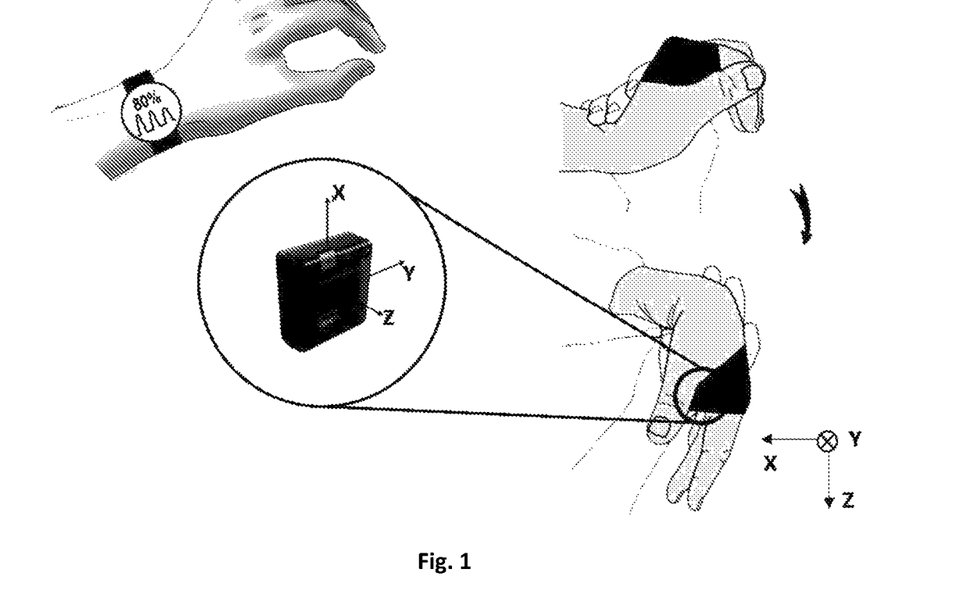
FIG. 1: Set up of the motion sensor and its placement on the hand during wrist rigidity assessment. The shown coordinate system is relative to the device, not the world.

It is disclosed a system comprising a small-sized wearable motion sensor and custom-made software to visualize the signal and evaluate wrist rigidity during DBS surgery, as shown in FIG. 1. The sensor is placed on the palm of the hand and held by a textile band, as depicted in FIG. 1. Such configuration does not interfere in the normal passive wrist flexion movement nor with the surgical procedure, while being favourable that the wrist flexion is performed along the sensor's Y-axis, i.e. the axis of rotation of the wrist for evaluating rigidity, independently from the hand pose.

According to an embodiment, to guarantee data invariance with respect to hand rotation and position, only gyroscope data, acquired with respect to the device coordinate system was considered, according to an embodiment. It may also be possible to convert accelerometer or magnetometer data, or combinations thereof with gyroscope data, to obtain a signal of angular velocity, though with added complexity.

The angular velocity signal was obtained as follows, where the number 32767 can take any value between −32768 and 32767, e.g. depending on the specific sensor resolution:

$$\omega = \frac{g_y}{32767} 2000 \; (°s^{-1}) \tag{1}$$

Where $g_y$ stands for the raw gyroscope Y-axis data. The signal was filtered using a 4-sample moving average filter to remove eventual tremor and then kept only samples corresponding to wrist flexion movements. For that, the absolute value of the negative arcades of $\omega$ was taken, discarding the remainder of the signal. Rigidity can be perceived as a resisting force or torque that limits the velocity, range and smoothness of the imposed wrist flexion movement. Therefore, a stimulation setting that diminishes rigidity yields higher angular velocities and smoother signals.

Figure 2A:
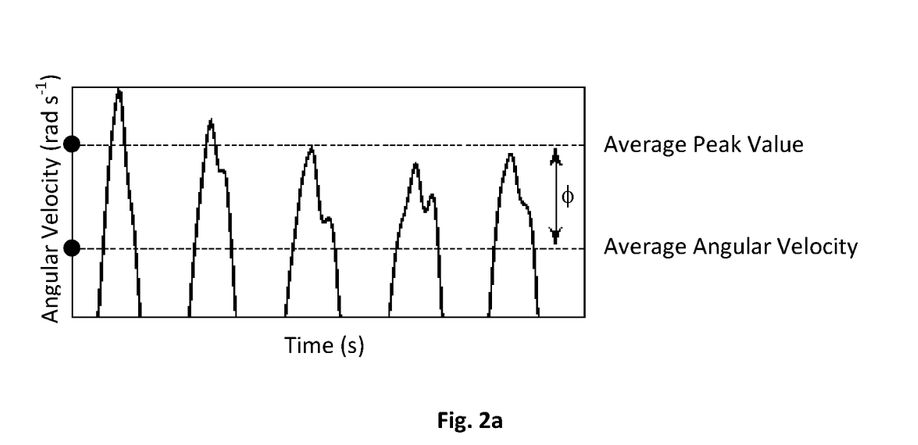
FIG. 2a: The average angular velocity (upper dotted line) and the average peak value (lower dotted line) were extracted to describe the kinematics of the passive wrist flexion movement. The range of possible values for the signal descriptor, φ is also represented.

It is disclosed a signal descriptor, i.e. a non-rigidity index, from quantitative kinematic measures, as show in FIG. 2a:

$$\phi = \sqrt{\mu_\omega \mu_P} \tag{2}$$

where $\mu_\omega$ stands for the average angular velocity and $\mu_P$ for the average peak value. Absolute peaks were calculated as the highest values between two valleys of the signal; within a margin of $0.2° \; s^{-1}$ according to an embodiment.

There is a direct correlation between a low rigidity and higher values of $\mu P$. However, that is not enough for an accurate description, since signals with widely different shapes can have peaks of similar height. Elongated signal arcades, few peaks in a certain period of time or unexpected plateaus during the flexion movement, even in signals with high amplitude, correspond to some residual rigidity and must be taken in consideration. Such information is yielded by $\mu\omega$, since the average value of the signal decreases for non-smooth and non-sharpen signals. The squared root notches back $\phi$ into the signal range and establishes an operating point whose value is between the two kinematic measures.

The descriptor was expected to significantly distinguish between the stimulation settings that alleviate the patients' condition and those who do not. Therefore, the training dataset was clustered into the specified classes and computed the values of $\phi$ for each signal. Jarque-Bera tests[8] confirmed the normality of the data and descriptive power was assessed using two-tailed t-tests.

Figure 2B:
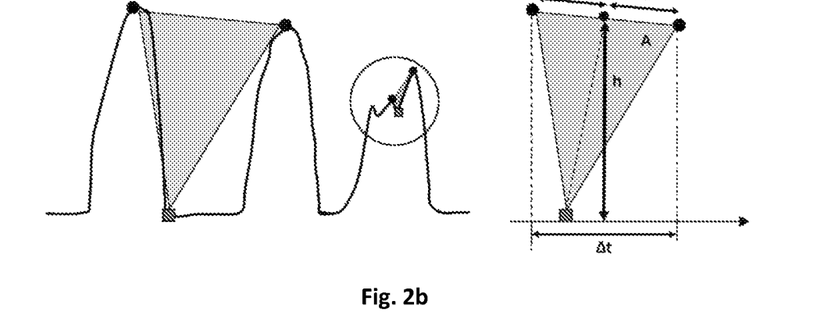
FIG. 2b: The cogwheel effect was detected using a geometric approach that defines triangles from fiducial points on the angular velocity signal. On the left, it is shown the difference between a smooth part of the signal (larger triangle) and a zone in which the cogwheel effect exists (smaller and tilted triangle). On the right, the features extracted from the drawn triangles are described.
Figure 2C:
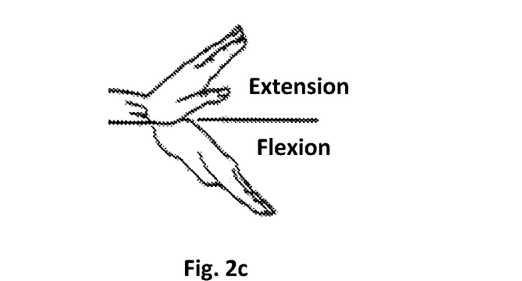
FIG. 2c: Schematic representation of the wrist articulation flexion-extension axis of rotation, corresponding to the mentioned y-axis.

The cogwheel rigidity of the wrist joint creates artefacts on the angular velocity signal, observable in FIG. 2b. Such artefacts correspond to non-minima valleys of the signal bordered by two peaks. For their detection, all the peaks and valleys of the signal were extracted, and drawn each possible triangle between a valley and the two peaks enclosing it. Smoother parts of the signal have larger triangles, defined between absolute minima and maxima, whereas the cogwheel parts lead to smaller, tilted triangles. The detection criterion is disclosed as follows:

$$\frac{h}{\Delta t \cdot A} \geq \lambda \quad (3)$$

where h stands for the distance between a valley and the midpoint between the flanking peaks, $\Delta t$ is the time span of the triangle, A its area and $\lambda$ the threshold value for the detection of a cogwheel artefact. We optimized $\lambda$ and assessed the detection accuracy from a ROC curve built following what is described in [9]: 30 randomly chosen training signals, whose ground-truth was previously agreed between observers.

The rigidity during passive wrist flexion was labelled by specialists following a discrete decimal scale ranging between 0 and 80 percent. Higher label values correspond to lower perceived wrist rigidity. Mathworks Matlab R2013a was used to analyse the 48 signals of the training set. Following this, the polynomial mathematical model that best approximates the perceived wrist rigidity as a function of the mean value of the signal descriptor $\phi$ for each rigidity scale was built. Approximations of higher degrees can lead to overfitting and be less responsive to widely different incoming signals. Moreover, although this problem could be addressed using standard machine learning techniques, they require heavy computation and would limit a future implementation with local signal processing. Training error was assessed as the Leave-One-Out Error.

According to an embodiment, signal shape descriptors and other kinematic properties, such as quaternions, are integrated into this classification model to guarantee higher robustness and discriminative power. According to a further embodiment, wrist rigidity is compared under each stimulation setting with the baseline rigidity. This allows to estimate how each setting alleviates wrist rigidity, diminishing the influence of inter-subject variability in rigidity. According to a further embodiment, this device and method can be used in other PD related medical procedures, such as tremor detection and characterization or levodopa tests.

The disclosure here presented has the potential to be a major breakthrough in its field. The evaluation of wrist rigidity during DBS surgery with reliability, with clinical relevance and real-time feedback to neurologists was mimicked. For that, a comfortable, simple and custom-made wearable motion sensor system was designed, capable of evaluating wrist rigidity under different stimulation settings using only angular velocity values computed from gyroscope data. It was correctly classified over 80% of the evaluated signals using a polynomial mathematical model and deriving a signal descriptor based on simple kinematic measures. The present device performance is not influenced by the possible variability of the imposed wrist flexion movement, and invariant hand position and orientation.

According to an embodiment, signal processing strategies to evaluate signal shape and smoothness are used, as well as incorporating quaternion information. The estimation of biomechanical properties from the acquired signals can be of major help to completely describe rigidity and provide fiducial information for the success of DBS. Additionally, according to an embodiment it is compared each signal to be evaluated with the baseline rigidity characteristics to accurately estimate the diminishing in perceived rigidity and monitor the alleviation of the condition.

It is disclosed an articulation rigidity assessment device for assessing the rigidity of an articulation when a bending motion is imposed to a limb of said articulation around a predetermined rotation axis of the articulation, said device comprising: a one-axis angular velocity sensor for attaching to said limb such that the axis of measurement is parallel to the axis of rotation of the imposed bending motion; a data processor configured (i.e. programmed) to process the signal of the angular velocity sensor and to distinguish between non-rigid and rigid states of the articulation using the processed angular velocity signal.

An embodiment comprises a skin-contacting patch for applying to the limb of the patient wherein the one-axis angular velocity sensor is attached to said skin-contacting patch.

In an embodiment, the articulation is a wrist articulation of the patient and the limb is the respective hand. In an embodiment, the axis of rotation of the imposed bending motion is the axis of rotation of extension-flexion of the wrist articulation.

In an embodiment, the skin-contacting patch is a skin-contacting patch for applying to the palm or back of the hand.

In an embodiment, the data processor is configured to calculate a non-rigidity index by the square root of the multiplication of the average of the angular velocity signal by the average peak value of the angular velocity signal.

In an embodiment, the data processor is configured to calculate a non-rigidity index for a cycle of the imposed bending motion by the square root of the multiplication of the average of the angular velocity signal by the average peak value of the angular velocity signal.

In an embodiment, the data processor is configured to distinguish between non-rigid and rigid states by detecting a non-rigid state if the calculated non-rigidity index is above a predetermined threshold.

In an embodiment, the data processor is configured to calculate a quantitative continuous scale of the rigidity of the articulation using a polynomial function whose input is the non-rigidity index.

In an embodiment, the data processor is configured to detect cogwheel rigidity of the articulation by detecting non-minima valleys bordered by two peaks of the non-rigidity index along a cycle of the imposed bending motion.

In an embodiment, the data processor is configured to detect cogwheel rigidity of the articulation by detecting non-minima valleys bordered by two peaks of the non-rigidity index by:

extracting all the peaks and valleys of the index signal along time;

drawing each possible triangle between a valley and the two peaks enclosing it;

determine if the following calculation is true:

$$\frac{h}{\Delta t \cdot A} \geq \lambda$$

wherein h is the distance between the valley and the midpoint between the two peaks, Δt is the time span of the triangle formed by the valley and the two peaks, A is the triangle area and λ is a predetermined threshold value for the detection of cogwheel rigidity.

In an embodiment, the one-axis angular velocity sensor is a one-axis gyroscope.

An embodiment comprises a three-axis gyroscope, wherein the one-axis angular velocity sensor is a virtual sensor, and the data processor is configured to calculate the equivalent one-axis angular velocity virtual sensor signal from the signals of the three-axis gyroscope.

An embodiment comprises an accelerometer-gyroscope-magnetometer, wherein the one-axis angular velocity sensor is a virtual sensor, and wherein the data processor is configured to calculate the equivalent one-axis angular velocity virtual sensor signal from the signals of the accelerometer-gyroscope-magnetometer.

In an embodiment, the data processor is configured to pre-process the angular velocity sensor signal by filtering the angular velocity sensor signal with a moving average of the absolute value of the signal.

In an embodiment, the skin-contacting patch is an adhesive patch.

It is also described a fingerless glove wherein the skin-contacting patch is an integral part of said glove.

It is also described an elastic textile band wherein the skin-contacting patch is an integral textile part of said band.

It is also described the use of the device for assisting in deep brain stimulation surgery of a patient.

An embodiment comprises a display attached to the data processor, wherein the data processor is connected wirelessly to the angular velocity sensor.

An embodiment comprises a display connected wirelessly to the data processor, wherein the data processor is electrically connected to the angular velocity sensor and the data processor is attached to the skin-contacting patch.

BRIEF DESCRIPTION OF THE DRAWINGS

The following figures provide preferred embodiments for the present disclosure and should not be seen as limiting the scope of the disclosure.

FIG. 2: Illustration of the signal processing strategies followed.

DETAILED DESCRIPTION

According to an embodiment, the designed hardware comprises a Texas Instruments Microcontroller (MCU), a Invensense's ITG-3200 gyroscope (range of ±2000°/s and 6.5 mA operating current), a KXTF9-1026 Kionix accelerometer (with ranges 2 g, 4 g and 8 g) and a Honeywell's HMC5883L magnetometer (with compass heading accuracy of 1° to 2°). The MCU gathers data from the sensors at 100 Hz, building packages that are transmitted via Bluetooth to a synced device at a 42 Hz rate, and can compute quaternions in real time.

The sensor signal was acquired and processed using National Instruments Labview 2014, in a Intel Core i7-4600U CPU @ 2.70 GHz computer, according to an embodiment.

Six patients (Mean Age: 67 years; 3 male and 3 female) subjected to bilateral DBS surgery were tested and a total of 48 signals was acquired to train a rigidity classification model. Medication was withdrawn for 12 h prior to the procedure and local anaesthetic was administered. The DBS electrodes were inserted in the STN stereotactic target and electrophysiological inspection was performed to determine the definitive stimulation site. Stimulation frequency was fixed at 130 Hz and both voltage and electrode position were varied, while searching for the greatest reduction in wrist rigidity during passive wrist flexion without secondary effects. The optimal setting was agreed between two experienced physicians. The patients wore the developed system during the whole procedure for signal recording purposes. Additional 4 patients (Mean Age: 64 years; 2 male and 2 female) had their rigidity classified under variable stimulation settings by the present disclosure. Patients were submitted to the same medical procedure as the training group. Signal classification (156 signals as total) performance was evaluated against the agreement of two expert physicians: classifications were accepted if contained inside a 5% margin with respect to the clinical score.

It is disclosed a device and method to quantitatively evaluate wrist rigidity and help on the determination of the optimal stimulation setting. The statistical analysis results, summarized in Table I demonstrated the capability of the selected kinematic measures φ to distinguish between rigid and non-rigid states. Furthermore, it was observed that φ has a slightly more discriminative ($p_\phi$=0.027) than its counterparts ($p_{\mu\omega}$=0.034 and $p_{\mu P}$=0.029). This confirms the present disclosure in that the combination of both features describes well the correlation between the signal amplitude and shape while maintaining the simplicity.

TABLE I

Both the selected kinematic measures and the signal descriptor are able to discriminate between rigid and non-rigid states (angular velocity values in °s$^{-1}$)

| Feature | Rigid | | Non-Rigid | | P-value |
|---|---|---|---|---|---|
| | Mean | Std | Mean | Std | |
| Average Angular Velocity | 3.33 | 0.58 | 5.62 | 1.51 | 0.034 |
| Average Peak Value | 12.9 | 3.13 | 29.9 | 6.60 | 0.029 |
| Signal Descriptor φ | 6.55 | 1.22 | 11.3 | 3.07 | 0.027 |

Figure 3A:
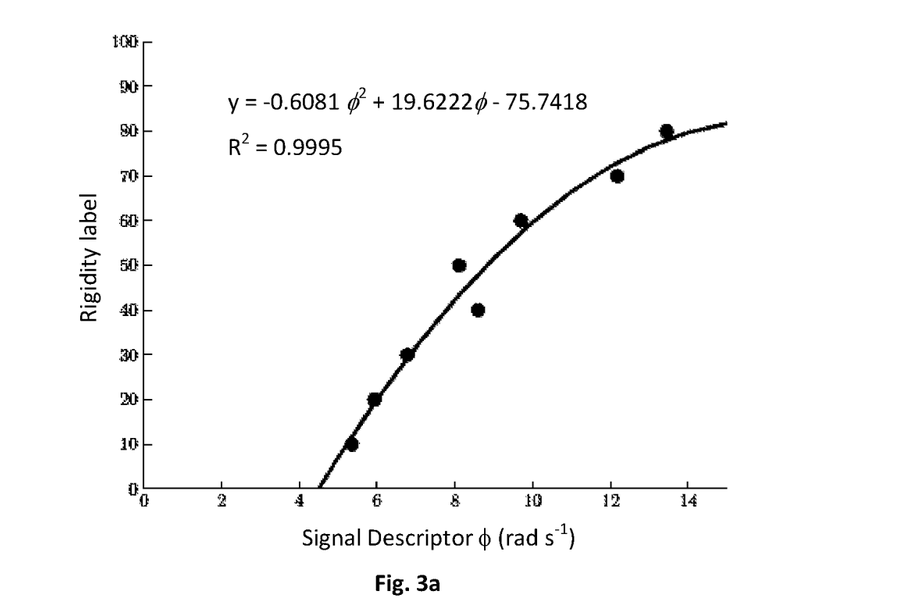
FIG. 3a: The polynomial function that best correlates the wrist rigidity and the average value of the signal descriptor—for each rigidity scale on the training dataset.

The derived mathematical model for rigidity classification, depicted in FIG. 3a, had high correlation with the data and presented a training error of 8.24±7.95%. This error range is acceptable, especially considering that a discrete scale is being modelled using a continuous function. Other relevant error source is the possibility of existing some undesired facilitation of the movement by patients.

Nevertheless, 131 out of 156 classifications performed by the present disclosure did not differ from the agreement between two expert physicians, corresponding to an acceptance rate above 80%. Major limitations were found on the evaluation of signals corresponding to intermediate rigidity states, whose correlation with the classification model was lower (see FIG. 3a). Conversely, the present disclosure detects more correctly low-rigidity states, meaning the optimal stimulation setting can be identified with low error. Such results suggest that the present disclosure can be a reliable second opinion on wrist rigidity evaluation (e.g., during DBS parameter trimming), with clinical benefits.

Additional biomechanical properties can also be explored in this context, such as work and impulse, both derived from resistive torque. However, these quantities are often dependent on the speed of the imposed movement which cannot be guaranteed by physicians.

In fact, such variability in the imposed velocity caused by the imposed movement by the physician can help to better perceive the wrist rigidity. A constant velocity would only be ensured by using a mechanical system attached to the limb, increasing the invasiveness and complexity of the procedure.

Figure 3B:
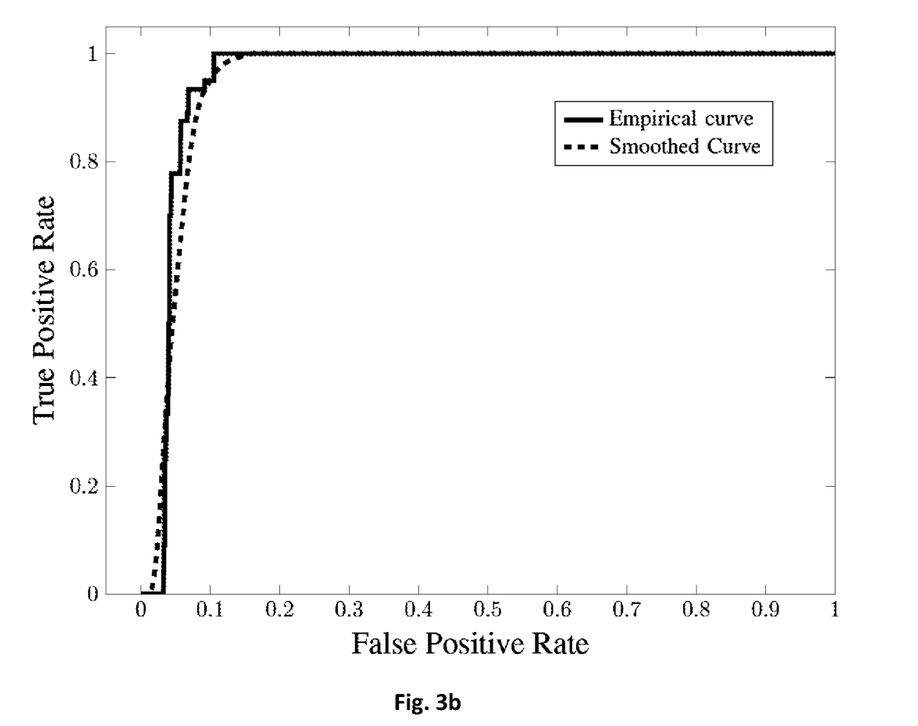
FIG. 3b: The ROC curve for the detection of cogwheel artefacts on the angular velocity signal. Optimal operating for λ=100.
Figure 4:
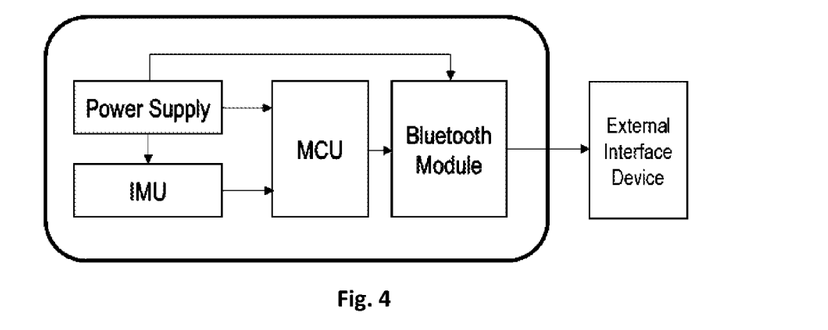
FIG. 4: Schematic representation depicting the main blocks of an embodiment, in which IMU represents an inertial measurement unit and MCU represents a microcontroller Unit.
Figure 5:
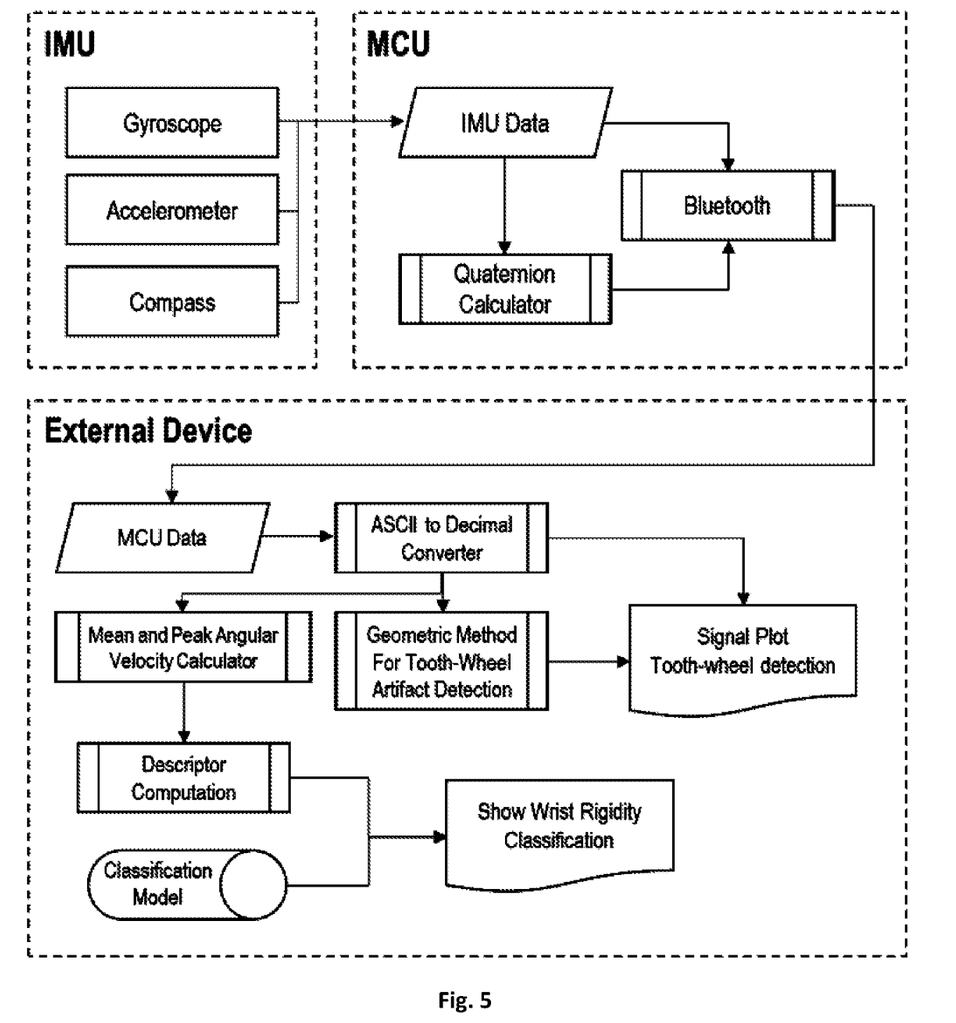
FIG. 5: Schematic representation depicting the data and work flow of an embodiment, in which IMU represents an inertial measurement unit and MCU represents a microcontroller Unit.

Regarding the detection of cogwheel rigidity, the ROC Curve on FIG. 3b suggests high sensitivity of the presently disclosed methodology while keeping the false positive rate low. The optimal operation point was obtained for λ=100, yielding a sensitivity of 0.93. These results, along with the low computational cost required for the arithmetic operations that create and characterize the computed triangles, enable a real-time detection of cogwheel artefacts and its quantification for rigidity classification purposes.

The term "comprising" whenever used in this document is intended to indicate the presence of stated features, integers, steps, components, but not to preclude the presence or addition of one or more other features, integers, steps, components or groups thereof. It is to be appreciated that certain embodiments of the disclosure as described herein may be incorporated as code (e.g., a software algorithm or program) residing in firmware and/or on computer useable medium having control logic for enabling execution on a computer system having a computer processor, such as any of the servers described herein. Such a computer system typically includes memory storage configured to provide output from execution of the code which configures a processor in accordance with the execution. The code can be arranged as firmware or software. If implemented using modules, the code can comprise a single module or a plurality of modules that operate in cooperation with one another to configure the machine in which it is executed to perform the associated functions, as described herein.

The disclosure should not be seen in any way restricted to the embodiments described and a person with ordinary skill in the art will foresee many possibilities to modifications thereof. The above described embodiments are combinable. The following claims further set out particular embodiments of the disclosure.

The invention claimed is:

1. An articulation rigidity assessment device for assessing the rigidity of an articulation when a bending motion is imposed to a limb of said articulation around a predetermined rotation axis of the articulation during deep brain stimulation (DBS) surgery in which at least one DBS electrode is advanced by a neurologist into the brain, said device comprising:
a single-axis angular velocity sensor for attaching to said limb such that the axis of measurement is parallel to the axis of rotation of the imposed bending motion; and
a data processor configured to:
process the signal of the angular velocity sensor,
distinguish between non-rigid and rigid states of the articulation using the processed angular velocity signal,
detect cogwheel rigidity of the articulation by detecting non-minima valleys bordered by two peaks of the angular velocity signal along a cycle of the imposed bending motion, and
output real-time feedback to the neurologist of an indication of a rigidity classification at the DBS electrode location.

2. The device according to claim 1, further comprising a skin-contacting patch, wherein the single-axis angular velocity sensor is attached to said skin-contacting patch.

3. The device according to claim 2, wherein the skin-contacting patch is a skin-contacting patch for applying to a palm or back of a hand.

4. The device according to claim 2, further wherein the skin-contacting patch is an adhesive patch.

5. The device according to claim 2, further comprising a fingerless glove wherein the skin-contacting patch is an integral part of said glove.

6. The device according to claim 2, further comprising an elastic textile band wherein the skin-contacting patch is an integral textile part of said band.

7. The device according to claim 1, wherein the articulation is a wrist articulation of a patient and the limb is the respective hand.

8. The device according to claim 1, wherein the axis of rotation of the imposed bending motion is the axis of rotation of extension-flexion of a wrist articulation.

9. The device according to claim 1, wherein the data processor is configured to calculate a non-rigidity index by the square root of the multiplication of the average of the angular velocity signal by the average peak value of the angular velocity signal.

10. The device according to claim 9, wherein the data processor is configured to distinguish between non-rigid and rigid states by detecting a non-rigid state if the calculated non-rigidity index is above a predetermined threshold.

11. The device according to claim 9, wherein the data processor is configured to calculate a quantitative continuous scale of the rigidity of the articulation using a polynomial function whose input is the non-rigidity index.

12. The device according to claim 1, wherein the data processor is configured to calculate a non-rigidity index for a cycle of the imposed bending motion by the square root of the multiplication of the average of the angular velocity signal by the average peak value of the angular velocity signal.

13. The device according to claim 1, wherein the configured data processor detects the non-minima valleys bordered by two peaks of the angular velocity signal by:
 extracting all the peaks and valleys of the angular velocity signal along time;
 drawing each possible triangle between a valley and the two peaks enclosing it; and
 determining if the following calculation is true:

$$\frac{h}{\Delta t \cdot A} \geq \lambda$$

wherein h is the distance between the valley and the midpoint between the two peaks, $\Delta t$ is the time span of the triangle formed by the valley and the two peaks, A is the triangle area and $\lambda$ is a predetermined threshold value for the detection of cogwheel rigidity.

14. The device according to claim 1, wherein the single-axis angular velocity sensor is a single-axis gyroscope.

15. The device according to claim 1, wherein the data processor is configured to pre-process the angular velocity sensor signal by filtering the angular velocity sensor signal with a moving average of the absolute value of the signal.

16. The device according to claim 1, further comprising a display attached to the data processor, wherein the data processor is connected wirelessly to the angular velocity sensor.

17. The device according to claim 1, further comprising a display connected wirelessly to the data processor, wherein the data processor is electrically connected to the angular velocity sensor and the data processor is attached to the skin-contacting patch.

* * * * *